US006689728B2

(12) United States Patent
Diez

(10) Patent No.: US 6,689,728 B2
(45) Date of Patent: Feb. 10, 2004

(54) COMPOSITE TRANSPARENT BAR SOAP CONTAINING VISIBLE SOAP INSERT(S)

(75) Inventor: Ricardo Diez, Paradise Valley, AZ (US)

(73) Assignee: The Dial Company, Scottsdale, AZ (US)

( * ) Notice: Subject to any disclaimer, the term of this patent is extended or adjusted under 35 U.S.C. 154(b) by 255 days.

(21) Appl. No.: 09/827,424

(22) Filed: Apr. 6, 2001

(65) Prior Publication Data

US 2003/0064901 A1 Apr. 3, 2003

(51) Int. Cl.[7] .................... A61K 7/50

(52) U.S. Cl. .................... 510/147; 510/151; 510/152; 510/153; 510/155; 510/156

(58) Field of Search .................... 510/141, 147, 510/151, 152, 153, 155, 156

(56) References Cited

U.S. PATENT DOCUMENTS

| | | | | |
|---|---|---|---|---|
| 1,827,549 | A | 10/1931 | Villain | |
| 3,413,230 | A | 11/1968 | Dupuis | 252/92 |
| 3,926,828 | A | 12/1975 | O'Neill et al. | 252/117 |
| 3,929,678 | A | 12/1975 | Laughlin et al. | 252/526 |
| 4,081,394 | A | 3/1978 | Bartley | 252/91 |
| 4,116,439 | A | 9/1978 | Chavarria et al. | 273/59 |
| 4,165,293 | A | 8/1979 | Gordon | 510/118 |
| 4,175,050 | A | 11/1979 | Carduck et al. | 252/91 |
| 4,182,737 | A | 1/1980 | Haber et al. | 265/135 |
| 4,347,270 | A | 8/1982 | Hart | 428/13 |
| 4,504,433 | A | 3/1985 | Inui et al. | 264/232 |
| 4,739,007 | A | 4/1988 | Okada et al. | 524/789 |
| 4,810,734 | A | 3/1989 | Kawasumi et al. | 523/216 |
| 4,894,411 | A | 1/1990 | Okada et al. | 524/710 |
| 5,002,685 | A | 3/1991 | Chambers et al. | 252/134 |
| 5,041,234 | A | 8/1991 | Instone et al. | 252/118 |
| 5,217,639 | A | 6/1993 | Mottola | 252/90 |
| 5,310,495 | A | 5/1994 | Hill et al. | 252/118 |
| 5,496,489 | A | 3/1996 | Dussault et al. | 252/134 |
| 5,703,025 | A | 12/1997 | Zyngier et al. | 510/147 |
| 5,786,311 | A | 7/1998 | Zyngier et al. | 510/147 |
| 5,856,283 | A | 1/1999 | Abbas et al. | 510/131 |
| 5,869,437 | A | 2/1999 | Wolfersberger | 510/147 |
| 5,993,371 | A | 11/1999 | White et al. | 511/147 |
| 6,147,040 | A | 11/2000 | van der Hagen | 510/146 |

FOREIGN PATENT DOCUMENTS

| | | |
|---|---|---|
| EP | 0 507 559 A2 | 10/1992 |
| EP | 0 548 814 A1 | 6/1993 |
| WO | WO 91 16412 | 10/1991 |
| WO | WO 93 04161 | 3/1993 |
| WO | WO 96 04360 | 2/1996 |
| WO | WO 98/11196 | 3/1998 |
| WO | WO 98 14559 | 4/1998 |

*Primary Examiner*—Necholus Ogden
(74) *Attorney, Agent, or Firm*—Marshall, Gerstein & Borun LLP

(57) ABSTRACT

A composition and a method of preparing a solid, transparent/translucent moisturizing/cosmetic/personal cleansing bar having one or more visible soap inserts, wherein a transparent soap matrix surrounding the soap insert has an increased melting temperature of at least 55° C. to prevent melting the soap insert during manufacture, and to reduce deformation during storage and handling, increasing its hardness and durability, and substantially reducing the tendency of the bar to lose weight over time by evaporation of water by exposure to room temperature. The soap insert can have the same composition as the surrounding transparent matrix soap, having less water to provide at least a 3° C. higher melting point, and/or a small percentage of pigment or dye, for easy recycling of defective bars, without the need to separate the soap insert from the surrounding matrix soap.

41 Claims, No Drawings

COMPOSITE TRANSPARENT BAR SOAP CONTAINING VISIBLE SOAP INSERT(S)

FIELD OF THE INVENTION

The present invention is directed to a composite soap article formed from a transparent or translucent molten matrix soap material that is poured to surround one or more solid soap inserts, said inserts formed from a higher melting point soap composition that is visibly differentiatible from the surrounding transparent matrix soap composition due to a difference in opacity and/or color. In a preferred embodiment, the insert soap composition differs from the surrounding soap composition only by water content and/or dye and/or pigment addition—the insert soap composition having less water than the surrounding soap composition in a preferred embodiment, making the insert composition more opaque and having a higher melting temperature than the surrounding transparent matrix soap composition.

BACKGROUND OF THE INVENTION AND PRIOR ART

Composite, decorative soaps, sometimes called mosaic soaps, are well known in the art as evidenced by the Inui et al. U.S. Pat. No. 4,504,433. These composite soaps are formed by placing one or more solid pieces of insert soap, in the form of a decoration, design, or written material, into a mold, holding the insert(s) in position within the mold and then pouring a solution of a melted transparent soap to fill the mold, thereby surrounding the insert(s). The transparent soap is generally poured into the mold to surround the inserts at temperatures in the range of about 60° C. to about 75° C. and the transparent soap then is cooled to solidify, thereby permanently holding the soap insert(s) in position.

The soap inserts, also known as icons, can be formed from various soap compositions, generally about 85% sodium stearate and 15% water, making an opaque soap, or can be formed from various other compositions such that the icons or inserts will be visibly distinguishable relative to the surrounding transparent matrix soap composition so that the icons or inserts are clearly visible within the composite bar of soap. It should be understood that the terms “insert” and “icon” are used interchangeably herein, however, “icon” should not be understood to require the insert soap composition to be formed in any definite or predetermined shape or size. The insert or icon soap composition can be any predetermined or random shape or size.

These decorative soap bars are very appealing and attractive from a visual standpoint but have a number of drawbacks, some of which result from the substantially different soap compositions used for the icons or inserts as compared to the composition of the surrounding transparent soap material. During use, the higher dissolution rate of the clear soap results in an uneven wearing of the soap bar—the matrix or clear soap dissolves in water about two to three times faster than icons made of regular sodium stearate-based, opaque soap. Further, during storage, often there is chemical migration from the clear matrix soap into the inserts at the insert/matrix interface, resulting in the softening of the inserts. In addition, although the decorative soap bars are normally wrapped in a protective polymeric film, the clear matrix soap loses weight at a higher rate than the surrounded soap inserts, thus distorting the appearance of the decorative bar of soap.

Another common problem with such decorative soaps is from dye “bleeding” which results from dye migration from the soap inserts into the surrounding transparent matrix soap composition. Further, recycling of any defective or unsold soap bars is virtually impossible with extant decorative bar soaps due to the substantially different compositions for the insert and matrix soaps.

Mottola U.S. Pat. No. 5,217,639 discloses a decorative soap bar that includes an opaque portion and a transparent portion—both portions adjoining each other only along a single curvilinear shaped surface—wherein the opaque and transparent soap compositions differ only by including a solid pigment in the opaque composition. However, the melting points of both soap compositions are the same so that one composition melts partially when contacted with the other soap composition during manufacture so that detailed icons or inserts are impossible.

SUMMARY OF THE INVENTION

In brief, the present invention is directed to a decorative bar of soap including one or more internal soap inserts, in any desired shape, surrounded and completely encased by a transparent or translucent matrix soap composition, wherein the surrounding matrix soap composition has a lower melting point than the icon or insert soap composition.

In accordance with a preferred embodiment of the present invention, the soap composition used to form the icons or inserts can be the same as that for the surrounding transparent matrix soap composition with the exception that the icon or insert soap composition must, in any manner, be made to be visually distinguishable from the surrounding or matrix soap composition, e.g., the insert is made less translucent or less transparent than the surrounding composition by virtue of having less water; having an increased concentration of insoluble soap; having an increase in the carbon length of the insoluble soap; having higher boiling solvent (s); containing a dye or pigment; and/or having higher melting point surfactant(s), but otherwise may contain the same components as the surrounding matrix soap composition. By including less water in the icon or insert soap composition, the icons or inserts may become readily visually distinguishable from the surrounding matrix soap composition, in being more opaque than the surrounding matrix soap composition, and the icons or inserts have a higher melting point, being at least 3° C. higher, than the surrounding matrix soap composition when formed with the components described hereinafter. In accordance with another important feature of the present invention, the increase in melting point of the icon soap composition can be affected by an expedient selected from the group consisting of: (1) a lower amount of water; (2) an increase in the insoluble soap content; (3) an increase in the carbon chain length of the insoluble soap; (4) solvents having a higher boiling point; and/or (5) different surfactant(s) causing a higher boiling point in the icon soap composition.

The above and other aspects and advantages of the present invention will become more apparent from the following detailed description of the preferred embodiments, taken in conjunction with the drawing.

BRIEF DESCRIPTION OF THE DRAWING

The FIGURE is a graph that compares the hardness, in Newtons, of the preferred translucent/transparent soap composition of the present invention (Example 6—PREFERRED) to the same composition containing 17.7% by weight water, prior to dehydration (Example 6—FORMED).

DETAILED DESCRIPTION OF THE PREFERRED EMBODIMENTS

The transparent/translucent matrix soap composition of the present invention includes polyhydric solvents, in an amount of about 15% to about 65% by weight, preferably about 25% to about 65% by weight, including (A) one or more polyhydric solvents that include at least three hydroxyl groups, in an amount of 5% by weight to about 40% by weight, and (B) one or more polyhydric solvents that include two hydroxyl groups, e.g., diols or glycols, in an amount of about 10% by weight to about 30% by weight. The transparent/translucent matrix soap composition contains about 4% to about 13% by weight water, preferably about 4% to about 12% water, most preferably about 7% to about 12% water, and preferably contains at least 1% by weight more water than the composition used to form the icons or inserts, with the icons or inserts having sufficiently less water than the surrounding composition so that the icons or inserts are visibly distinguishable from the surrounding composition.

The transparent/translucent surrounding matrix soap composition contains a final water content of about 13% by weight or less, preferably about 4% to about 12%, more preferably about 7% to about 12% water, to prevent melting and reduce deformation during storage and handling, increasing its hardness and durability, and substantially reducing the tendency of the decorative bar to lose weight over time by evaporation of water by evaporation.

Accordingly, one aspect of the present invention is to provide a decorative transparent/translucent moisturizing/cosmetic/personal cleansing bar that is more durable, has a relatively high melting point, and a lower water content than prior art personal cleansing bars, while maintaining clarity (transparency) for visibility of one or more internal shaped inserts.

Another aspect of the present invention is to provide a decorative transparent/translucent moisturizing/cosmetic/personal cleansing bar that is less susceptible to being deformed by heat and/or pressure and includes a combination of polyhydric solvents (1) having three or more hydroxyl groups; and (2) two hydroxyl groups, while providing a bar having a minimum amount of water (4–13% by weight) so that hydrolyzable bar components, such as antibacterial components, e.g., triclocarban (TCC), maintain more of their efficacy for longer periods of time.

A further aspect of the present invention is to provide a decorative cleansing bar having one or more visually detectable shaped inserts formed from a soap composition that approximates a surrounding transparent/translucent matrix soap composition, wherein the insert composition is more opaque, or otherwise visually distinguishable from the surrounding soap composition, but preferably dissolves in water at approximately the same rate as the surrounding soap composition.

Still another aspect of the present invention is to provide a decorative cleansing bar that includes one or more shaped icons or inserts that have a composition that differs from a surrounding transparent/translucent composition essentially only in water content and/or dye or pigment addition so that decorative cleansing bars that are imperfect during manufacture can be recycled easily either to an insert composition supply vessel or to a transparent/translucent matrix soap composition supply vessel, without separating the inserts from the surrounding matrix soap composition prior to recycling.

The transparent/translucent surrounding matrix soap composition of the present invention includes the following components, after manufacture, and may contain additional additives, such as antibacterial agents, dyes, perfumes, fillers, polymers, silicones, encapsulated materials, and the like:

| | Range % | Preferred % | More Preferred % | Most Preferred % |
|---|---|---|---|---|
| water-soluble polyhydric solvent(s), | 15–65 | 25–65 | 30–55 | 35–50 |
| $3^{+}$-OH, e.g., glycerine, sugar alcohols, e.g., sorbitol and the like | 5–35 | 10–30 | 15–25 | 17–22 |
| 2-OH, e.g., propylene glycol, polyethylene glycol, dipropylene glycol | 10–30 | 15–30 | 20–30 | 22–27 |
| monohydric alcohol, e.g., ethanol | 0–4 | 0.5–3 | 0.5–2 | 0.75–1.5 |
| soap | 5–40 | 8–30 | 10–25 | 10–15 |
| surfactant(s) | 5–40 | 5–30 | 8–25 | 10–20 |
| water | 4–13 | 4–12 | 7–12 | 10–12 |

The term "soap", for purposes of describing the "soap" component of both the transparent/translucent matrix soap composition and the icon or insert composition of the present invention, has the meaning as normally understood by those skilled in the art: monovalent salts of fatty monocarboxylic acids having a carbon chain length of from 12 to 24, preferably from 14 to 18 carbon atoms. These monovalent salts would normally be sodium salts, although some cations, such as K, Mg or alkanolammonium ions could be used. The preferred insoluble fatty acid soap is at least 90% by weight, more preferably at least 95% by weight selected from the group consisting of sodium myristate, sodium palmitate, sodium stearate and mixtures of any two or more thereof. Other insoluble soaps, particularly higher fatty acid insoluble soaps, can also be used.

The preferred surrounding transparent/translucent matrix soap composition of the present invention is melted and poured to surround one or more solid insert, shaped soap compositions.

The transparent/translucent surrounding matrix soap compositions of this invention can be prepared with reduced water content, for example, by using anhydrous polyhydric alcohols and/or anhydrous surfactants or by removing water from the composition initially formed with a higher water content.

Significant performance improvements for the transparent/translucent surrounding matrix soap composition are obtained by combining water-soluble polyhydric solvents having at least three hydroxyl groups ($3^{+}$-OH) with water-soluble polyhydric solvents having two hydroxyl groups (2-OH). Significant performance improvements also are obtained by reducing the water content to a maximum of about 13% by weight, preferably in the range of about 4% to about 12% by weight, more preferably about 7% to about 12% by weight, most preferably about 10% to about 12% by weight water. The melting point of the matrix soap composition is increased to at least 55° C., which is above the temperatures that are expected to be reached during shipping and storage, thus avoiding melting and deformation of the decorative personal cleansing bars of the present invention.

Another benefit to the transparent/translucent surrounding matrix soap composition of the present invention is the reduction of weight loss. A cleansing bar containing about 20% by weight water loses about 17% of its original weight when exposed to room temperature (25° C.) for three weeks, whereas the decorative cleansing bars of the present invention, including a transparent/translucent surrounding composition with a water content of 10% by weight only loses about 7.5% of its original weight under the same conditions.

Surfactants

The transparent/translucent surrounding matrix soap composition of the present invention includes about 5% to about 40% by weight surfactants, preferably about 5% to about 30% by weight, more preferably about 8% to about 25%, most preferably about 10% to about 20% by weight surfactants.

The surfactant can be an anionic surfactant, a cationic surfactant, a nonionic surfactant, an ampholytic or amphoteric surfactant or a compatible mixture of surfactants.

Suitable anionic surfactants include, but are not limited to, compounds in the classes known as alkyl sulfates, alkyl ether sulfates, alkyl ether sulfonates, sulfate esters of an alkylphenoxy polyoxyethylene ethanol, alpha-olefin sulfonates, beta-alkoxy alkane sulfonates, alkylaryl sulfonates, alkyl monoglyceride sulfates, alkyl monoglyceride sulfonates, alkyl carbonates, alkyl ether carboxylates, fatty acids, sulfosuccinates, sarcosinates, oxtoxynol or nonoxynol phosphates, taurates, fatty taurides, fatty acid amide polyoxyethylene sulfates, isethionates, or mixtures thereof. Additional anionic surfactants are listed in McCutcheon's Emulsifiers and Detergents, 1993 Annuals, (hereafter McCutcheon's), McCutcheon Division, MC Publishing Co., Glen Rock, N.J., pp. 263–266, incorporated herein by reference. Numerous other anionic surfactants, and classes of anionic surfactants, are disclosed in Laughlin et al. U.S. Pat. No. 3,929,678, incorporated herein by reference.

The transparent/translucent surrounding matrix soap compositions of the present invention also can contain nonionic surfactants. Typically, a nonionic surfactant has a hydrophobic base, such as a long chain alkyl group or an alkylated aryl group, and a hydrophilic chain comprising a sufficient number (i.e., 1 to about 30) of ethoxy and/or propoxy moieties. Examples of classes of nonionic surfactants include ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$–$C_{18}$) acids, condensation products of ethylene oxide with long chain amines or amides, and mixtures thereof. Fatty alcohol ethoxylates (FAE) are preferred for dissolving antibacterial compounds, such as triclocarban (TCC).

Exemplary nonionic surfactants include, but are not limited to, methyl gluceth-10, PEG-20 methyl glucose distearate, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$–$C_{22}$) alcohol, including 3 to 20 ethylene oxide moieties, polyoxyethylene-20 isohexadecyl ether, polyoxyethylene-23 glycerol laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxyethylene-6 tridecyl ether, laureth-2, laureth-3, laureth-4, PEG-3 castor oil, PEG 600 dioleate, PEG 400 dioleate, and mixtures thereof.

Numerous other nonionic surfactants are disclosed in McCutcheon's Detergents and Emulsifiers, 1993 Annuals, published by McCutcheon Division, MC Publishing Co., Glen Rock, N.J., pp. 1–246 and 266–272; in the *CTFA International Cosmetic Ingredient Dictionary, Fourth Ed.*, Cosmetic, Toiletry and Fragrance Association, Washington, D.C. (1991) (hereinafter the CTFA Dictionary) at pages 1–651; and in the *CTFA Handbook*, at pages 86–94, each incorporated herein by reference.

In addition to anionic and nonionic surfactants, cationic, ampholytic, and amphoteric surfactants can be used in the cleansing bars of the present invention. Cationic surfactants include amine oxides, for example.

Ampholytic surfactants can be broadly described as derivatives of secondary and tertiary amines having aliphatic radicals that are straight chain or branched, and wherein one of the aliphatic substituents contains from about 8 to 18 carbon atoms and at least one of the aliphatic substituents contains an anionic water-solubilizing group, e.g., carboxy, sulfonate, or sulfate. Examples of compounds falling within this description are sodium 3-(dodecylamino)propionate, sodium 3-(dodecylamino)-propane-1-sulfonate, sodium 2-(dodecylamino)ethyl sulfate, sodium 2-(dimethylamino) octadecanoate, disodium 3-(N-carboxymethyl-dodecylamino)propane-1-sulfonate, disodium octadecyliminodiacetate, sodium 1-carboxymethyl-2-undecylimidazole, and sodium N,N-bis(2-hydroxyethyl)-2-sulfato-3-dodecoxypropylamine.

More particularly, one class of ampholytic surfactants include sarcosinates and taurates having the general structural formula

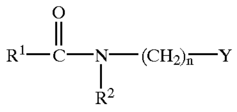

wherein $R^1$, for the above, as well as the following classes of ampholytic surfactants, is $C_{11}$ through $C_{21}$ alkyl, $R^2$ is hydrogen or $C_1$–$C_2$ alkyl, Y is $CO_2M$ or $SO_3M$, M is an alkali metal, and n is a number 1 through 3.

Another class of ampholytic surfactants is the amide sulfosuccinates having the structural formula

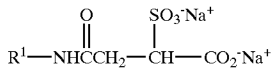

The following classes of ampholytic surfactants also can be used:

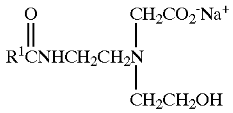

alkoamphoglycinates

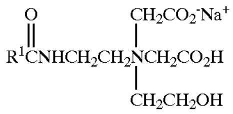

alkoamphocarboxyglycinates

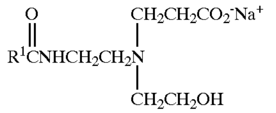

alkoamphopropionates

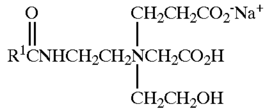

alkoamphocarboxypropionates

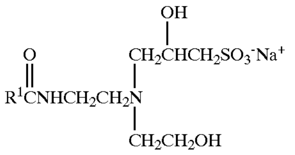

alkoamphopropylsulfonates

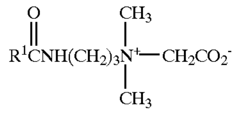

alkamidopropyl betaines

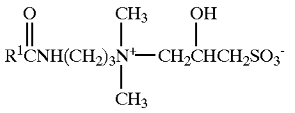

alkamidopropyl hydroxysultaine

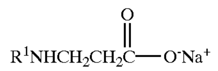

alkylaminopropionates

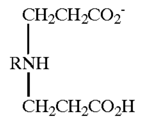

alkyliminopropionates.

Additional classes of ampholytic surfactants include the phosphobetaines and the phosphitaines.

Specific, nonlimiting examples of ampholytic surfactants useful in the soap compositions used to make the decorative cleansing bars of the present invention are sodium coconut N-methyl taurate, sodium oleyl N-methyl taurate, sodium tall oil acid N-methyl taurate, sodium palmitoyl N-methyl taurate, cocodimethylcarboxymethylbetaine, lauryldimethylcarboxymethylbetaine, lauryldimethylcarboxyethylbetaine, cetyldimethylcarboxymethylbetaine, lauryl-bis-(2-hydroxyethyl) carboxymethylbetaine, oleyldimethylgammacarboxypropylbetaine, lauryl-bis-(2-hydroxypropyl) carboxyethylbetaine, cocoamidodimethylpropylsultaine, stearylamidodimethylpropylsultaine, laurylamido-bis-(2-hydroxyethyl)propylsultaine, disodium oleamide PEG-2 sulfosuccinate, TEA oleamido PEG-2 sulfosuccinate, disodium oleamide MEA sulfosuccinate, disodium oleamide MIPA sulfosuccinate, disodium ricinoleamide MEA sulfosuccinate, disodium undecylenamide MEA sulfosuccinate, disodium wheat germamido MEA sulfosuccinate, disodium wheat germamido PEG-2 sulfosuccinate, disodium isostearamideo MEA sulfosuccinate, cocoamphoglycinate, cocoamphocarboxyglycinate, lauroamphoglycinate, lauroamphocarboxyglycinate, capryloamphocarboxyglycinate, cocoamphopropionate, cocoamphocarboxypropionate, lauroamphocarboxypropionate, capryloamphocarboxypropionate, dihydroxyethyl tallow glycinate, cocamido disodium 3-hydroxypropyl phosphobetaine, lauric myristic amido disodium 3-hydroxypropyl phosphobetaine, lauric myristic amido glyceryl phosphobetaine, lauric myristic amido carboxy disodium 3-hydroxypropyl phosphobetaine, cocoamido propyl monosodium phosphitaine, lauric myristic amido propyl monosodium phosphitaine, and mixtures thereof.

Polyhydric Solvents(s):

The transparent/translucent surrounding soap compositions of the present invention comprises from about 15% to about 65% by weight, preferably about 25% to about 65% by weight, more preferably from about 30% to about 55% by weight, most preferably about 35% to about 50% by weight of a combination of water-soluble polyhydric organic solvents including (A) about 5% to about 35% by weight water-soluble polyhydric solvent(s) having three or more hydroxyl groups ($3^+$-OH), and (B) about 10% to about 30% by weight polyhydric solvent(s) having two hydroxyl groups (2-OH). Preferred water soluble organic polyols having two hydroxyl groups (2-OH) include those selected from the group consisting of: propylene glycol; dipropylene glycol; butylene glycol; ethylene glycol; 1,7-heptanediol; monoethylene glycols, polyethylene glycols, polypropylene glycols of up to 8,000 molecular weight; mono-$C_{1-4}$ alkyl ethers of any of the foregoing; and mixtures thereof. Preferred water-soluble polyhydric solvents that have at least three hydroxyl groups ($3^+$-OH) include glycerine, and any sugar alcohol, such as sorbitol.

Examples of suitable sugar alcohols include:

Tetritols:

Erythritol, threitol, D-threitol, L-threitol, and D,L-threitol.

Pentitols:

Ribitol, arabinitol, D-arabinitol, L-arabinitol, D,L-arabinitol and xylitol.

Hexitols:

Allitol, dulcitol (galacitol), glucitol, sorbitol, (D-glucitol), L-glucitol, D,L-glucitol, D-mannitol, L-mannitol, D,L-mannitol, altritol, D-altritol, L-altritol, D,L-altritol, iditol, D-iditol, and L-iditol.

Disaccharide alcohols:

Maltitol, lactitol and isomalt.

Soap

The fatty acid soap used in both the transparent/translucent matrix surrounding soap composition and in the icon-insert soap composition of the present invention comprises sodium soaps. However, low levels of non-sodium soaps such as potassium, magnesium, and/or triethanolammonium (TEA) soaps are permissible. Such non-sodium soaps, when used, are preferably used at a level of from 0% to 10% by weight, preferably from 0% to 5% by weight of the surrounding soap composition.

Optional Ingredients

The transparent/translucent surrounding matrix soap composition, as well as in the icon/insert soap composition of the present invention also can contain optional ingredients well known to persons skilled in the art. Such optional ingredients typically are present, individually, from 0% to about 5%, by weight, of the composition, and, collectively, from 0% to about 20%, by weight, of the composition.

Suitable optional ingredients include dyes, fragrances and one or more antibacterial compounds(s), that are present in a sufficient amount to perform their intended function and do not substantially adversely affect the transparency of the composition.

Classes of optional ingredients include, but are not limited to, dyes, fragrances, pH adjusters, thickeners, fillers, viscosity modifiers, buffering agents, foam stabilizers, antioxidants, foam enhancers, chelating agents, opacifiers, sanitizing or anti-microbial agents, preservatives, polymers, silicones, encapsulated materials, and similar classes of optional ingredients known to persons skilled in the art.

Specific classes of optional ingredients include alkanolamides as foam boosters and stabilizers; gums and polymers as thickening agents; inorganic phosphates, sulfates, and carbonates as buffering agents; EDTA and phosphates as chelating agents; and acids and bases as pH adjusters.

Examples of preferred classes of basic pH adjusters are ammonia; mono-, di-, and tri-alkyl amines; mono-, di-, and tri-alkanolamines; alkali metal and alkaline earth metal hydroxides; and mixtures thereof. However, the identity of the basic pH adjuster is not limited, and any basic pH adjuster known in he art can be used. Specific, nonlimiting examples of basic pH adjusters are ammonia; sodium, potassium, and lithium hydroxide; monoethanolamine; triethylamine; isopropanolamine; diethanolamine; and triethanolamine.

Examples of preferred classes of acidic pH adjusters are the mineral acids and polycarboxylic acids. Nonlimiting examples of mineral acids are hydrochloric acid, nitric acid, phosphoric acid, and sulfuric acid. Nonlimiting examples of polycarboxylic acids are citric acid, glycolic acid, and lactic acid. The identity of the acidic pH adjuster is not limited and any acidic pH adjuster known in the art, alone or in combination, can be used.

In accordance with a preferred embodiment of manufacturing the decorative moisturizing/cosmetic/personal cleansing bars of the present invention, the solvents and surfactants used in the matrix soap composition are added in an open agitated reaction vessel at atmospheric pressure and at a temperature sufficient to melt the fatty acids, generally at least about 70° C., e.g., 70° C. to 80° C. The fatty acid(s) then are added, followed by raising the temperature to at least about 80° C., e.g., 80–90° C., prior to the addition of a neutralizing agent, preferably a sodium base, e.g., NaOH, in an amount sufficient to provide 100% neutralization of the fatty acids, to form the soap, in situ. It should be understood that the soap, i.e., sodium myristate, sodium palmitate, and/or sodium stearate, can be added in pre-manufactured form instead of being formed, in situ. At this stage of the manufacturing process, if the water content matrix soap composition of the mixture is above 13% by weight, the temperature of the reaction mixture is raised to at least about 90° C., preferably 90° C. to 100° C. to evaporate sufficient water to provide a matrix soap composition having 4–13% by weight water, most preferably about 10–12% by weight water. It should be noted that during the above-described water evaporation or dehydration step of the manufacturing process, a small portion of the propylene glycol or other relatively low boiling solvents may evaporate together with the water. However, it has been found in the following examples that only about 0.5–2.0% of the propylene glycol is lost via evaporation during the dehydration step, and such solvent evaporation can be compensated for by the initial addition of 0.5–2.0% extra propylene glycol or other relatively low boiling polyhydric solvents at any stage of manufacture.

It should also be noted that the above-described dehydration step is unnecessary if one or more of the solvents and/or surfactants is added in anhydrous form (see Examples 3, 4, 7 and 10). Further, the dehydration step can be carried out at much lower temperatures by using a sealed reaction vessel at a pressure below atmospheric (under vacuum).

As well known in the art, the more volatile optional ingredients, such as dyes, fragrances and monohydric alcohols, should be added to the composition after cooling the molten matrix soap composition, e.g., to 70° C. or below, so that the volatile components are not lost to evaporation.

The decorative cleansing bars of the present invention can be manufactured by adding the soap in sodium salt form, or the fatty acid(s) can be added together with a sodium base, such as sodium hydroxide to form the soap in situ. As shown in the following examples, the matrix soap composition of the decorative moisturizing/cosmetics cleansing bars of the present invention have sufficient clarity to provide at least 85% light transmission, generally 85–95% light transmission. The inserts or icons should have a light transmission that is visually distinguishable from the surrounding transparent/translucent matrix soap composition, e.g., at least 1% lower light transmission, or having a different color. In accordance with another important feature of the present invention, when the bars are frozen and then thawed (Freeze/Thaw), the clarity of the matrix soap composition remains at least 90%, preferably at least 95% of its original clarity compared to about 80% clarity after Freeze/Thaw of prior art transparent soap compositions containing 17.7% water (see Example 6—PREFERRED vs. Example 6—FORMED). The following examples show the surrounding transparent/translucent soap compositions in percentages by weight of materials added to an agitated reaction vessel designated as "ADDED"; the composition formed from the materials added, designated "FORMED"; and the final composition after removal of water, if any, designated "FINAL":

In the following examples of transparent/translucent matrix soap compositions, when the transparent/translucent matrix soap composition is made in situ by reaction of fatty acid(s) with a caustic solution, e.g., NaOH, it is preferred to add the caustic solution before the addition of the fatty acid(s) to prevent formation of gels or lumps, which would increase manufacturing time. It has also been found that color degradation is minimized by adding any sorbitol, or other non-reducing sugars containing at least three hydroxyl groups, only when the percent free fatty acid(s) is in the range of about 0.1% to about 2%, preferably in the range of 0.2% to 1.5%, more preferably in the range of 0.5% to 1.0% free fatty acid(s), based on the total weight of free fatty acids and neutralized fatty acids. The following is the preferred sequence of addition:

1) Mix the non-sorbitol polyhydric solvent(s), e.g., propylene glycol and glycerine and the surfactant(s);

2) Raise batch temperature to 70 to 80° C.;
3) Add less than the required amount of the caustic solution needed to fully neutralize the later-added fatty acids, e.g., about 95% of the required amount of caustic solution, e.g., NaOH;
4) Add the fatty acids, ensuring that the temperature remains above about 80° C. but below 100° C.;
5) Analyze for free fatty acid, e.g., titrate with NaOH, using an indicator, such as a dye, and adjust, if required, to 0.1 to 2.0% by weight, preferably 0.2 to 1.5% (most preferred 0.5% to 1.0%) based on the total weight of free fatty acids and neutralized fatty acids, as lauric acid, adding more caustic solution or more fatty acid, e.g., stearic acid;
6) Add the sorbitol solution, if sorbitol is one of the polyhydric solvents, and mix well;
7) Start the water evaporation step, e.g., by raising the temperature of the batch to about 99 to 102° C. with good agitation while preventing the batch from boiling. Of course, water removal under reduced pressure would require lower temperatures, the temperature depending upon the degree of applied vacuum;
8) When the desired amount of water has been removed, cool the batch to 75 to 80° C.

Matrix Soap Composition Examples

EXAMPLE 1

| | | |
|---|---|---|
| ADDED | | |
| Propylene Glycol | 22.8 | |
| Glycerine | 15.3 | |
| Sorbitol (70%) | 15.8 | |
| Sorbitol (100%) | 0.0 | |
| SLES (70%) | 12.0 | |
| AOS* (40%) | 0.0 | |
| FAE** (100%) | 0.0 | |
| Myristic acid | 7.3 | |
| Stearic acid | 11.1 | |
| $H_2O$ | 9.9 | |
| NaOH (50%) | 5.8 | |
| TOTAL | 100.0 | |
| FORMED | | |
| Propylene Glycol | 22.8 | |
| Glycerine | 15.3 | |
| Sorbitol (100%) | 11.1 | |
| SLES (100%) | 8.4 | |
| AOS* (100%) | 0.0 | |
| FAE** (100%) | 0.0 | |
| NaMyristate | 8.0 | |
| NaStearate | 12.0 | |
| Total Water | 22.5 | |
| TOTAL | 100.0 | |
| CLARITY 86/90 | | |
| MELTING POINT (° C.) 50 | | |
| FINAL | | |
| $H_2O$ Removed | 13.0 | |
| Propylene Glycol | 26.2 | Polyhydric Solvents: 54.5% |
| Glycerine | 17.6 | 2-OH: 26.2% |
| Sorbitol | 12.7 | $3^+$-OH: 28.3% |
| SLES | 9.7 | |
| AOS* | 0.0 | |
| FAE** | 0.0 | |
| NaMyristate | 9.2 | |
| NaStearate | 13.8 | |
| Final Water | 10.9 | |
| TOTAL | 100.1 | |
| CLARITY 84/90 | | |
| MELTING POINT (° C.) 60 | | |

*alpha olefin sulfonate
**fatty alcohol ethoxylate

EXAMPLE 2

| Dry Sorbitol (no need to remove water) | | |
|---|---|---|
| ADDED | | |
| Propylene Glycol | 26.0 | |
| Glycerine | 17.0 | |
| Sorbitol (70%) | 0.0 | |
| Sorbitol (100%) | 13.7 | |
| SLES (70%) | 12.7 | |
| AOS* (40%) | 0.0 | |
| FAE** (100%) | 0.0 | |
| Myristic acid | 10.0 | |
| Stearic acid | 12.7 | |
| $H_2O$ | 0.0 | |
| NaOH (50%) | 7.3 | |
| TOTAL | 99.4 | |
| FORMED | | |
| Propylene Glycol | 26.0 | |
| Glycerine | 17.0 | |
| Sorbitol (100%) | 13.7 | |
| SLES (100%) | 8.9 | |
| AOS* (100%) | 0.0 | |
| FAE** (100%) | 0.0 | |
| NaMyristate | 11.0 | |
| NaStearate | 13.7 | |
| Total Water | 9.1 | |
| TOTAL | 99.4 | |
| FINAL | | |
| $H_2O$ Removed | 0 | |
| Propylene Glycol | 26.0 | Polyhydric Solvents: 56.7% |
| Glycerine | 17.0 | 2-OH: 26.0% |
| Sorbitol | 13.7 | $3^+$-OH: 30.7% |
| SLES | 8.9 | |
| AOS* | 0.0 | |
| FAE** | 0.0 | 8.9 Surfactants |
| NaMyristate | 11.0 | |
| NaStearate | 13.7 | 24.7 Soap |
| Final Water | 9.1 | 9.1 Water |
| TOTAL | 99.4 | 99.4 Total |
| CLARITY 85/90 | | |
| MELTING POINT (° C.) 60 | | |

*alpha olefin sulfonate
**fatty alcohol ethoxylate

EXAMPLE 3

| High Level Of Surfactant | |
|---|---|
| ADDED | |
| Propylene Glycol | 20.4 |
| Glycerine | 5.0 |
| Sorbitol (70%) | 0.0 |
| Sorbitol (100%) | 10.6 |
| SLES (70%) | 13.4 |
| AOS* (40%) | 0.0 |
| FAE** (100%) | 25.0 |
| Myristic acid | 8.5 |
| Stearic acid | 10.8 |
| $H_2O$ | 0.0 |
| NaOH (50%) | 6.2 |
| TOTAL | 99.9 |
| FORMED | |
| Propylene Glycol | 20.4 |
| Glycerine | 5.0 |
| Sorbitol (100%) | 10.6 |

-continued

| High Level Of Surfactant | | |
|---|---|---|
| SLES (100%) | 9.4 | |
| AOS* (100%) | 0.0 | |
| FAE** (100%) | 25.0 | |
| NaMyristate | 9.3 | |
| NaStearate | 11.7 | |
| Total Water | 8.5 | |
| TOTAL | 99.9 | |
| FINAL | | |
| $H_2O$ Removed | 0 | |
| Propylene Glycol | 20.4 | Polyhydric Solvents: 36.0% |
| Glycerine | 5.0 | 2-OH: 20.4% |
| Sorbitol | 10.6 | $3^+$-OH: 15.6% |
| SLES | 9.4 | |
| AOS* | 0.0 | |
| FAE** | 25.0 | 34.4 Surfactants |
| NaMyristate | 9.3 | |
| NaStearate | 11.7 | 21.0 Soap |
| Final Water | 8.5 | 8.5 Water |
| TOTAL | 99.9 | 99.9 TOTAL |
| CLARITY 82/90 | | |
| MELTING POINT (° C.) 62 | | |

*alpha olefin sulfonate
**fatty alcohol ethoxylate

EXAMPLE 4

| Very Low Water Content, Low Foaming Cleanser | | |
|---|---|---|
| ADDED | | |
| Propylene Glycol | 26.1 | |
| Glycerine | 17.2 | |
| Sorbitol (70%) | 0.0 | |
| Sorbitol (100%) | 12.6 | |
| SLES (70%) | 0.0 | |
| AOS* (40%) | 0.0 | |
| FAE** (100%) | 12.4 | |
| Myristic acid | 10.6 | |
| Stearic acid | 13.4 | |
| $H_2O$ | 0.0 | |
| NaOH (50%) | 7.7 | |
| TOTAL | 100.0 | |
| FORMED | | |
| Propylene Glycol | 26.1 | |
| Glycerine | 17.2 | |
| Sorbitol (100%) | 12.6 | |
| SLES (100%) | 0.0 | |
| AOS* (100%) | 0.0 | |
| FAE** (100%) | 12.4 | |
| NaMyristate | 11.6 | |
| NaStearate | 14.5 | |
| Total Water | 5.6 | |
| TOTAL | 100.0 | |
| FINAL | | |
| $H_2O$ Removed | 0 | |
| Propylene Glycol | 26.1 | Polyhydric Solvents: 55.9% |
| Glycerine | 17.2 | 2-OH: 26.1% |
| Sorbitol | 12.6 | $3^+$-OH: 29.8% |
| SLES | 0.0 | |
| AOS* | 0.0 | |
| FAE** | 12.4 | 12.4 Surfactants |
| NaMyristate | 11.6 | |
| NaStearate | 14.5 | 26.1 Soap |
| Final Water | 5.6 | 5.6 Water |
| TOTAL | 100.0 | 100.0 TOTAL |
| CLARITY 84/90 | | |
| MELTING POINT (° C.) 62 | | |

*alpha olefin sulfonate
**fatty alcohol ethoxylate

EXAMPLE 5

| PEG-2ME | | |
|---|---|---|
| ADDED | | |
| Propylene Glycol | 16.4 | |
| Glycerine | 0.0 | |
| Sorbitol (70%) | 19.5 | |
| Sorbitol (100%) | 0.0 | |
| PEG-2ME* | 10.4 | |
| SLES (70%) | 19.6 | |
| AOS** (40%) | 0.0 | |
| FAE*** (100%) | 0.0 | |
| Myristic acid | 11.0 | |
| Stearic acid | 14.1 | |
| $H_2O$ | 0.0 | |
| NaOH (50%) | 8.0 | |
| Ethanol | 1.0 | |
| TOTAL | 100.0 | |
| FORMED | | |
| Propylene Glycol | 16.4 | |
| Glycerine | 0.0 | |
| Sorbitol (100%) | 13.7 | |
| PEG-2ME* | 10.4 | |
| SLES (100%) | 13.7 | |
| AOS** (100%) | 0.0 | |
| FAE*** (100%) | 0.0 | |
| NaMyristate | 12.1 | |
| NaStearate | 15.2 | |
| Ethanol | 1.0 | |
| Total Water | 17.6 | |
| TOTAL | 100.0 | |
| FINAL | | |
| $H_2O$ Removed | 7.0 | |
| Propylene Glycol | 17.6 | Polyhydric Solvents: 43.5% |
| Glycerine | 0.0 | 2-OH: 28.8% |
| Sorbitol | 14.7 | $3^+$-OH: 14.7% |
| PEG-2ME* | 11.2 | |
| SLES | 14.8 | |
| AOS** | 0.0 | |
| FAE*** | 0.0 | 14.8 Surfactants |
| NaMyristate | 13.0 | |
| NaStearate | 16.4 | 29.4 Soap |
| Ethanol | 1.0 | |
| Final Water | 11.3 | 11.3 Water |
| TOTAL | 100.0 | 100.0 TOTAL |
| CLARITY 83/90 | | |
| MELTING POINT (° C.) 62 | | |

*polyethylene 2 glycol methyl ether
**alpha olefin sulfonate
***fatty alcohol ethoxylate

EXAMPLE 6

| (Preferred Embodiment) | |
|---|---|
| ADDED | |
| Propylene Glycol | 25.1 |
| Glycerine | 6.0 |
| Sorbitol (70%) | 18.4 |
| Sorbitol (100%) | 0.0 |
| SLES (70%) | 18.4 |
| AOS* (40%) | 0.0 |
| FAE** (100%) | 0.0 |
| Myristic acid | 10.3 |
| Stearic acid | 13.1 |
| $H_2O$ | 1.2 |
| NaOH (50%) | 7.5 |
| TOTAL | 100.0 |
| FORMED | |
| Propylene Glycol | 25.1 |
| Glycerine | 6.0 |
| Sorbitol (100%) | 12.9 |
| SLES (100%) | 12.9 |
| AOS* (100%) | 0.0 |
| FAE** (100%) | 0.0 |
| NaMyristate | 11.3 |
| NaStearate | 14.2 |
| Total Water | 17.7 |
| TOTAL | 100.0 |

| FINAL | PREFERRED | | | | | |
|---|---|---|---|---|---|---|
| $H_2O$ Removed | 5.0 | | 7.5 | | 10.0 | |
| Propylene Glycol | 26.4 | Polyhydric | 27.1 | Polyhydric | 27.9 | Polyhydric |
| Glycerine | 6.3 | Solvents: 46.3% | 6.5 | Solvents: 47.5% | 6.7 | Solvents: 47.9% |
| Sorbitol | 13.6 | 2-OH: 26.4% | 13.9 | 2-OH: 27.1% | 14.3 | 2-OH: 27.9% |
| | | $3^+$-OH: 19.9% | | $3^+$-OH: 20.4% | | $3^+$-OH: 20.0% |
| SLES | 13.6 | | 13.9 | | 14.3 | |
| AOS* | 0.0 | | 0.0 | | 0.0 | |
| FAE** | 0.0 | | 0.0 | | 0.0 | |
| NaMyristate | 11.9 | | 12.2 | | 12.5 | |
| NaStearate | 14.9 | | 15.3 | | 15.7 | |
| Final Water | 13.3 | | 11.0 | | 8.5 | |
| TOTAL | 100.0 | | 100.0 | | 100.0 | |

| FORMED | 0% $H_2O$ REMOVED | 5% $H_2O$ REMOVED | 7.5% $H_2O$ REMOVED | 10.0% $H_2O$ REMOVED |
|---|---|---|---|---|
| CLARITY | 85/90 | 83/90 | 81/90 | 79/90 |
| MELTING POINT (° C.) | 50 | 56 | 62 | 64 |
| HARDNESS (N) | 16.2 | | 22.5 | |
| Freeze/Thaw | 72/90 | | 78/80 | |
| Weight Loss | 10% | | 4% | |

*alpha olefin sulfonate
**fatty alcohol ethoxylate

EXAMPLE 7

| Dry Sorbitol (no need to remove water) | |
|---|---|
| ADDED | |
| Propylene Glycol | 27.1 |
| Glycerine | 6.5 |
| Sorbitol (70%) | 0.0 |
| Sorbitol (100%) | 13.9 |
| SLES (70%) | 18.6 |
| AOS* (40%) | 0.0 |
| FAE** (100%) | 0.0 |
| Myristic acid | 11.3 |

-continued

| Dry Sorbitol (no need to remove water) | |
|---|---|
| Stearic acid | 14.4 |
| $H_2O$ | 0.0 |
| NaOH (50%) | 8.2 |
| TOTAL | 100.0 |
| FORMED | |
| Propylene Glycol | 27.1 |
| Glycerine | 6.5 |
| Sorbitol (100%) | 13.9 |
| SLES (100%) | 13.0 |

-continued

| Dry Sorbitol (no need to remove water) | | |
|---|---|---|
| AOS* (100%) | 0.0 | |
| FAE** (100%) | 0.0 | |
| NaMyristate | 12.4 | |
| NaStearate | 15.6 | |
| Total Water | 11.5 | |
| TOTAL | 100.0 | |
| FINAL | | |
| $H_2O$ Removed | 0 | |
| Propylene Glycol | 27.1 | Polyhydric Solvents: 47.5% |
| Glycerine | 6.5 | 2-OH: 27.1% |
| Sorbitol | 13.9 | $3^+$-OH: 20.4% |
| SLES | 13.0 | |
| AOS* | 0.0 | |
| FAE** | 0.0 | 13.0 Surfactants |
| NaMyristate | 12.4 | |
| NaStearate | 15.6 | 28.0 Soap |
| Final Water | 11.5 | 11.5 Water |
| TOTAL | 100.0 | 100.0 TOTAL |
| CLARITY 81/90 | | |
| MELTING POINT (° C.) 60 | | |

*alpha olefin sulfonate
**fatty alcohol ethoxylate

EXAMPLE 8

| | | |
|---|---|---|
| ADDED | | |
| Propylene Glycol | 24.3 | |
| Glycerine | 5.7 | |
| Sorbitol (70%) | 17.5 | |
| Sorbitol (100%) | 0.0 | |
| SLES (70%) | 14.3 | |
| AmphoAcetate (30%) | 8.6 | |
| FAE* (100%) | 0.0 | |
| Myristic acid | 9.9 | |
| Stearic acid | 12.6 | |
| $H_2O$ | 0.0 | |
| NaOH (50%) | 7.2 | |
| TOTAL | 100.1 | |
| FORMED | | |
| Propylene Glycol | 24.3 | |
| Glycerine | 5.7 | |
| Sorbitol (100%) | 12.3 | |
| SLES (100%) | 10.0 | |
| AmphoAcetate (100%) | 2.6 | |
| FAE* (100%) | 0.0 | |
| NaMyristate | 10.9 | |
| NaStearate | 13.6 | |
| Total Water | 20.8 | |
| TOTAL | 100.1 | |
| FINAL | | |
| $H_2O$ Removed | 9.0 | |
| Propylene Glycol | 26.7 | Polyhydric Solvents: 46.4% |
| Glycerine | 6.3 | 2-OH: 26.7% |
| Sorbitol | 13.5 | $3^+$-OH: 19.8% |
| SLES | 11.0 | |
| AmphoAcetate (100%) | 2.8 | |
| FAE* | 0.0 | 13.8 Surfactants |
| NaMyristate | 11.9 | |

-continued

| | | |
|---|---|---|
| NaStearate | 15.0 | 26.9 Soap |
| Final Water | 12.9 | 12.9 Water |
| TOTAL | 100.1 | 100.1 TOTAL |
| CLARITY 81/90 | | |
| MELTING POINT (° C.) 62 | | |

*fatty alcohol ethoxylate

EXAMPLE 9

| | | |
|---|---|---|
| ADDED | | |
| Propylene Glycol | 22.4 | |
| Glycerine | 5.1 | |
| Sorbitol (70%) | 16.0 | |
| Sorbitol (100%) | 0.0 | |
| SLES (70%) | 0.0 | |
| AOS* (40%) | 29.4 | |
| FAE** (100%) | 0.0 | |
| Myristic acid | 9.0 | |
| Stearic acid | 11.5 | |
| $H_2O$ | 0.0 | |
| NaOH (50%) | 6.6 | |
| TOTAL | 100.0 | |
| FORMED | | |
| Propylene Glycol | 22.4 | |
| Glycerine | 5.1 | |
| Sorbitol (100%) | 11.2 | |
| SLES (100%) | 0.0 | |
| AOS* (100%) | 11.8 | |
| FAE** (100%) | 0.0 | |
| NaMyristate | 9.9 | |
| NaStearate | 12.4 | |
| Total Water | 27.2 | |
| TOTAL | 100.0 | |
| FINAL | | |
| $H_2O$ Removed | 18.0 | |
| Propylene Glycol | 27.3 | Polyhydric Solvents: 47.2% |
| Glycerine | 6.2 | 2-OH: 27.3% |
| Sorbitol | 13.7 | $3^+$-OH: 19.9% |
| SLES | 0.0 | |
| AOS* | 14.3 | |
| FAE** | 0.0 | |
| NaMyristate | 12.0 | |
| NaStearate | 15.2 | |
| Final Water | 11.2 | |
| TOTAL | 99.9 | |
| CLARITY 81/90 | | |
| MELTING POINT (° C.) 58 | | |

*alpha olefin sulfonate
**fatty alcohol ethoxylate

EXAMPLE 10

| High Soap Level-Added In Pellet Form (as Na salt) | |
|---|---|
| ADDED | |
| Propylene Glycol | 24.1 |
| Glycerine | 5.8 |
| Sorbitol (70%) | |
| Sorbitol (100%) | 12.6 |
| SLES (70%) | 17.0 |
| AOS* (40%) | 0.0 |
| Soap Pellets (75%)** | 10.0 |
| Myristic acid | 10.1 |
| Stearic acid | 13.0 |

-continued

| High Soap Level-Added In Pellet Form (as Na salt) | | |
|---|---|---|
| $H_2O$ | 0.0 | |
| NaOH (50%) | 7.4 | |
| TOTAL FORMED | 100.0 | |
| Propylene Glycol | 24.1 | |
| Glycerine | 6.5 | |
| Sorbitol (100%) | 12.6 | |
| SLES (100%) | 11.9 | |
| AOS* (100%) | 0.0 | |
| Soap | 7.5 | |
| NaMyristate | 11.1 | |
| NaStearate | 14.1 | |
| Total Water | 12.0 | |
| TOTAL FINAL | 99.7 | |
| $H_2O$ Removed | 2.0 | |
| Propylene Glycol | 24.6 | Polyhydric Solvents: 44.1% |
| Glycerine | 6.6 | 2—OH: 24.6% |
| Sorbitol | 12.9 | $3^+$ —OH: 19.5% |
| SLES | 12.1 | |
| AOS* | 0.0 | 12.1 Surfactants |
| FAE**** | 7.7 | |
| NaMyristate | 11.3 | |
| NaStearate | 14.3 | 33.3 Soap |
| Final Water | 10.2 | 10.2 Water |
| TOTAL | 99.7 | 99.7 TOTAL |
| CLARITY 78/90 | | |
| MELTING POINT (° C.) 62 | | |

*alpha olefin sulfonate
**$C_{12}$ 0.2%
$C_{14}$ 3.0%
$C_{16}$ 31.0%
$C_{18}$ 16.0%
***$C_{18-1}$ 45.0%
***$C_{18-2}$ 4.0%
***$C_{18-3}$ 1.0%
***number of double bonds in $C_{18}$ acid
****fatty alcohol ethoxylate The following Examples 11–16 are examples of five different ways (Examples 12–16) that the insert soap composition can be varied from the matrix (surrounding transparent or translucent) soap composition (Example 11) to provide an insert soap composition that is visually distinguishable from the matrix soap composition, and have a melting point that is at least 3° C. higher than the matrix soap composition.

| | Example 11 MATRIX Reference composition | Example 12 INSERT Reduced water | Example 13 INSERT Increased insoluble soap | Example 14 INSERT Higher carbon chain length soap | Example 15 INSERT Higher BP solvents | Example 16 INSERT Different Surfactant |
|---|---|---|---|---|---|---|
| COMPOSITIONS ADDED | | | | | | |
| P Glycol | 26.3 | 26.3 | 26.3 | 26.3 | 10.0 | 26.3 |
| Di P Glycol | 0.0 | 0.0 | 0.0 | 0.0 | 22.0 | 0.0 |
| Glycerine | 6.0 | 6.0 | 6.0 | 6.0 | 0.0 | 17.2 |
| Sorbitol (70%) | 18.4 | 18.4 | 13.7 | 18.1 | 18.4 | 0.0 |
| Sorbitol (100%) | 0.0 | 0.0 | 0.0 | 0.0 | 0.0 | 12.6 |
| SLES (70%) | 18.4 | 18.4 | 13.5 | 18.1 | 18.4 | 0.0 |
| FAE (100%) | 0.0 | 0.0 | 0.0 | 0.0 | 0.0 | 12.4 |
| Myristic | 10.3 | 10.3 | 13.5 | 0.0 | 10.3 | 10.6 |
| Stearic | 13.1 | 13.1 | 17.2 | 24.3 | 13.1 | 13.4 |
| Water | 0.0 | 0.0 | 0.0 | 0.0 | 0.0 | 0.0 |
| NaOH (50%) | 7.5 | 7.5 | 9.8 | 7.2 | 7.5 | 7.7 |
| TOTAL COMPOSITION FORMED | 100.00 | 100.0 | 100.0 | 100.0 | 99.7 | 100.2 |
| P Glycol | 26.3 | 26.3 | 26.3 | 26.3 | 10.0 | 26.3 |
| Di P Glycol | 0.0 | 0.0 | 0.0 | 0.0 | 22.0 | 0.0 |
| Glycerine | 6.0 | 6.0 | 6.0 | 6.0 | 0.0 | 17.2 |
| Sorbitol (100%) | 12.9 | 12.9 | 9.6 | 12.7 | 12.9 | 12.6 |
| SLES (100%) | 13.4 | 13.4 | 9.8 | 13.1 | 13.4 | 0.0 |
| FAE (100%) | 0.0 | 0.0 | 0.0 | 0.0 | 0.0 | 12.4 |
| NaMyristate | 11.3 | 11.3 | 14.8 | 0.0 | 11.3 | 11.6 |
| NaStearate | 14.2 | 14.2 | 18.6 | 26.3 | 14.2 | 14.5 |
| Total Water | 15.8 | 15.8 | 14.8 | 15.4 | 15.8 | 5.6 |
| TOTAL COMPOSITION FINAL | 99.8 | 99.8 | 99.9 | 99.8 | 99.5 | 100.2 |
| Weight Loss | 3.5 | 5.5 | 2.5 | 3.0 | 3.5 | 0.0 |
| P Glycol | 27.3 | 27.8 | 27.0 | 27.1 | 10.4 | 26.3 |
| Di P Glycol | 0.0 | 0.0 | 0.0 | 0.0 | 22.8 | 0.0 |
| Glycerine | 6.2 | 6.3 | 6.2 | 6.2 | 0.0 | 17.2 |
| Sorbitol | 13.3 | 13.6 | 9.8 | 13.1 | 13.3 | 12.6 |
| SLES | 13.8 | 14.1 | 10.1 | 13.5 | 13.8 | 0.0 |

-continued

| | Example 11 MATRIX Reference composition | Example 12 INSERT Reduced water | Example 13 INSERT Increased insoluble soap | Example 14 INSERT Higher carbon chain length soap | Example 15 INSERT Higher BP solvents | Example 16 INSERT Different Surfactant |
|---|---|---|---|---|---|---|
| FAE | 0.0 | 0.0 | 0.0 | 0.0 | 0.0 | 12.4 |
| NaMyristate | 11.7 | 11.9 | 15.2 | 0.0 | 11.7 | 11.6 |
| NaStearate | 14.7 | 15.0 | 19.1 | 27.1 | 14.7 | 14.5 |
| Final Water | 12.8 | 10.9 | 12.6 | 12.8 | 12.8 | 5.6 |
| TOTAL | 99.8 | 99.8 | 99.9 | 99.8 | 99.5 | 100.2 |
| FINAL COMPOSITION AND PROPERTIES | | | | | | |
| Total solvents | 46.8 | 47.8 | 43.0 | 46.4 | 46.5 | 56.1 |
| 2 OH | 27.3 | 27.8 | 27.0 | 27.1 | 33.2 | 26.3 |
| $3^+$ OH | 19.6 | 20.0 | 16.0 | 19.2 | 13.3 | 29.8 |
| Surfactants | 13.8 | 14.1 | 10.1 | 13.5 | 13.8 | 12.4 |
| Soap | 26.4 | 26.9 | 34.3 | 27.1 | 26.4 | 26.1 |
| Water | 12.8 | 10.9 | 12.6 | 12.8 | 12.8 | 5.6 |
| Clarity | 83/90 | 81/90 | 76/90 | 75/90 | 79/90 | 84/90 |
| Melting Point, ° C. | 56 | 62 | 68 | 69 | 64 | 62 |

What is claimed is:

1. A decorative cleansing bar comprising a transparent or translucent surrounding soap composition that surrounds a solid of a soap composition that is visually distinguishable from the surrounding soap composition, both the surrounding soap composition and the icon soap composition comprising a combination of soap; water-soluble polyhydric solvents; surfactants; and water, wherein the surrounding soap composition has about 13% by weight water or less, has a melting point at least 3° C. lower than the melting point of the icon soap composition, and the surrounding soap composition has a melting point of at least 55° C.

2. The decorative cleansing bar of claim 1, wherein the soap composition differs from the surrounding soap composition essentially only based on one or more of the following:

(1) a lower amount of water;

(2) solvents having a higher boiling point;

(3) an increase in the insoluble soap content;

(4) different surfactant(s), having a higher boiling point, causing a higher melting point in the icon soap composition; and/or (5) an increase in the carbon chain length of the insoluble soap.

3. The decorative cleansing bar of claim 1, wherein the surrounding soap composition has a water content of 13% by weight or less, and the icon soap composition has a water content of 12% by weight or less.

4. The decorative cleansing bar of claim 1, wherein the surrounding soap composition has a water content that is at least 1% by weight greater than the water content of the icon soap composition, and the icon soap composition has a melting point at least 3° C. higher than the surrounding soap composition.

5. The decorative cleansing bar of claim 4, wherein the surrounding soap composition differs from the icon soap composition essentially only in water content.

6. The decorative cleansing bar of claim 4, wherein the surrounding soap composition has a water content of about 4% to about 13% by weight, and said icon soap composition has a water content of 3% to about 12% by weight.

7. The decorative cleansing bar of claim 4, wherein both the surrounding soap composition and the icon soap composition include, by weight:

15–65% water-soluble polyhydric solvents, including about 5% to about 35% having three or more hydroxyl groups, and about 10% to about 30% having two hydroxyl groups;

5–40% soap; and

5–40% surfactants.

8. The decorative cleansing bar of claim 7, wherein the surrounding and icon soap compositions include, by weight:

25–65% of said polyhydric solvents, including about 10% to about 30% having three or more hydroxyl groups, and about 15% to about 30% having two hydroxyl groups;

8–30% soap; and

5–30% surfactants.

9. The decorative cleansing bar of claim 8, wherein the surrounding and icon soap compositions include, by weight:

30–55% of said polyhydric solvents, including about 15% to about 25% having three or more hydroxyl groups, and about 20% to about 30% having two hydroxyl groups;

10–25% soap; and

8–25% surfactants.

10. The decorative cleansing bar of claim 9, wherein the surrounding and icon soap compositions include, by weight:

35–50% of said polyhydric solvents, including about 17% to about 22% having three or more hydroxyl groups, and about 22% to about 27% having two hydroxyl groups;

10–15% soap; and

10–20% surfactants.

11. The decorative cleansing bar of claim 10, wherein the surrounding soap composition comprises about 8% to about 12% by weight water.

12. A solid decorative cleansing bar comprising a transparent/translucent surrounding soap composition having a melting point of at least 55° C. that surrounds a solid icon of a soap composition that is visually distinguishable from the surrounding transparent/translucent soap composition, said transparent/translucent surrounding soap composition comprising, by weight:

15–65% water-soluble polyhydric solvents, including about 5% to about 35% having three or more hydroxyl groups, and about 10% to about 30% having two hydroxyl groups;

5–40% soap;

5–40% surfactants; and

4–13% water.

13. The solid decorative bar of claim 12, said transparent/translucent surrounding soap composition further including a monohydric alcohol in an amount of 4% by weight or less.

14. The solid decorative bar of claim 12, wherein said transparent/translucent surrounding soap composition comprises, by weight:

25–65% of said polyhydric solvents, including about 10% to about 30% having three or more hydroxyl groups, and about 15% to about 30% having two hydroxyl groups;

8–30% soap;

5–30% surfactants; and

7–12% water.

15. The solid decorative bar of claim 14, said transparent/translucent surrounding soap composition further including a monohydric alcohol in an amount of 0.5–3%.

16. The solid decorative bar of claim 14, wherein said transparent/translucent surrounding soap composition comprises, by weight:

30–55% of said polyhydric solvents, including about 15% to about 25% having three or more hydroxyl groups, and about 20% to about 30% having two hydroxyl groups;

10–25% soap;

8–25% surfactants; and

8–12% water.

17. The solid decorative bar of claim 16, said transparent/translucent surrounding soap composition further including a monohydric alcohol in an amount of 0.5–2%.

18. The solid decorative bar of claim 16, wherein said transparent/translucent surrounding soap composition comprises, by weight:

35–50% of said polyhydric solvents, including about 17% to about 22% having three or more hydroxyl groups, and about 22% to about 27% having two hydroxyl groups;

10–15% soap;

10–20% surfactants; and

10–12% water.

19. The solid decorative bar of claim 18, said transparent/translucent surrounding soap composition further including a monohydric alcohol in an amount of 0.75–1.5%.

20. The solid decorative bar of claim 12, wherein the soap is at least 90% selected from the group consisting of sodium myristate, sodium palmitate, sodium stearate, and mixtures thereof.

21. The solid decorative bar of claim 20, wherein the soap is at least 95% by weight saturated.

22. The solid decorative bar of claim 12, further including in a total concentration less than 20% by weight total, and less than 5% individually, additives selected from the group consisting of dyes, fragrances, antibacterial compounds, pH adjusters, thickeners, fillers, viscosity modifiers, buffering agents, foam stabilizers, antioxidants, foam enhancers, chelating agents, anti-microbial agents, preservatives, polymers, silicones, encapsulated materials, and mixtures thereof.

23. The solid decorative bar of claim 20, wherein the decorative cleansing bar contains an antibacterial compound.

24. A method of making a transparent, pour molded, solid, decorative soap bar containing one or more visible solid soap inserts comprising the steps of:

(a) mixing water-soluble polyhydric solvents; surfactants; soap; and water, at a temperature sufficient to form a molten mixture;

(b) disposing a solid soap insert into a shaped mold;

(c) disposing the molten mixture in the shaped mold to surround the solid soap insert; and (d) allowing the molten mixture to cool and solidify to form said decorative bar, wherein the surrounding soap composition has a melting point at least 2° C. lower than the solid soap insert.

25. The method of claim 24, wherein the molten mixture comprises:

15–65% by weight water-soluble polyhydric solvents, including about 5% to about 35% having three or more hydroxyl groups, and about 10% to about 30% having two hydroxyl groups;

5–40% by weight surfactants;

5–40% by weight soap; and at least 4% by weight water.

26. The method of claim 25, wherein at least one component of the bar, selected from the group consisting of a water-soluble polyhydric solvent and a surfactant, is added to the mixture in anhydrous form, such that the mixture is 13% by weight or less water.

27. The method of claim 25, wherein the soap is formed in situ by the addition of fatty acids and a base to form the sodium salt of the fatty acids.

28. The method of claim 25, wherein the water content of the molten mixture comprises greater than 13% to 30% by weight water, and the molten mixture is dehydrated before or after disposing the mixture in the shaped mold, to a water content of 13% by weight or less.

29. The method of claim 24, wherein the molten mixture comprises:

25–65% by weight of said polyhydric solvents, including about 10% to about 30% having three or more hydroxyl groups, and about 15% to bout 30% having two hydroxyl groups;

5–40% by weight soap;

5–40% by weight surfactants; and more than 13% by weight water, and the method includes a dehydration step.

30. The method of claim 24, wherein the molten mixture comprises:

15–65% by weight of said polyhydric solvents;

5–40% by weight soap;

5–40% by weight surfactants; and

4–13% by weight water, without a dehydration step.

31. The method of claim 29, wherein the molten mixture further includes a monohydric alcohol in an amount of 4% by weight or less.

32. The method of claim 29, wherein the water content of the mixture comprises more than 12% by weight water to about 30% by weight water, and the method includes a dehydration step.

33. The method of claim 24, wherein the molten mixtures comprises:

30–55% by weight of said polyhydric solvents, including about 15% to about 25% having three or more hydroxyl groups, and about 20% to about 30% having two hydroxyl groups;

8–30% by weight soap;

5–30% by weight surfactants; and more than 13% by weight water, and the method includes a dehydration step.

34. The method of claim 24, wherein the molten mixture comprises:

35–50% by weight of said polyhydric solvents, including about 17% to about 22% having three or more hydroxyl groups, and about 22% to about 27% having two hydroxyl groups;

8–30% by weight soap;

5–30% by weight surfactants; and

7–13% by weight water, without a dehydration step.

35. The method of claim 31, wherein the amount of monohydric alcohol is 0.5% to about 3% by weight of the mixture.

36. The method of claim 24, wherein the mixture comprises:

30–55% of said polyhydric solvents, including about 15% to about 25% having three or more hydroxyl groups, and about 20% to about 30% having two hydroxyl groups;

10–25% soap;

8–25% surfactants; and more than 13% by weight water, and the method includes a dehydration step.

37. The method of claim 36, wherein the mixture further includes 0.5–2% by weight of a monohydric alcohol.

38. The method of claim 24, wherein the mixture comprises:

40–55% by weight of said polyhydric solvents;

10–25% by weight soap;

8–25% by weight surfactants; and

8–13% by weight water, without a dehydration step.

39. The method of claim 38, wherein the mixture includes a monohydric alcohol in an amount of 0.5–2% by weight.

40. The method of claim 24, wherein the mixture comprises:

35–50% of said polyhydric solvents;

10–15% soap;

10–20% surfactants; and more than 13% by weight water, and the method includes a dehydration step.

41. The method of claim 24, wherein the mixing step is performed in accordance with the following sequence of steps:

(1) mixing the non-sorbitol polyhydric solvents with the surfactants;

(2) heating the mixture to about 70 to 80° C.;

(3) adding an alkali to neutralize later-added fatty acid;

(4) adding the fatty acid;

(5) analyzing for free fatty acid;

(6) adjusting the amount of free fatty acid to the range of about 0.1% to about 2%, based on the total weight of free fatty acids, and neutralized fatty acids by the addition of more alkali or more fatty acid;

(7) adding sorbitol; and (8) adding sufficient caustic to neutralize the free fatty acids.

* * * * *

UNITED STATES PATENT AND TRADEMARK OFFICE

CERTIFICATE OF CORRECTION

PATENT NO. : 6,689,728 B2
DATED : February 10, 2004
INVENTOR(S) : Ricardo Diez

It is certified that error appears in the above-identified patent and that said Letters Patent is hereby corrected as shown below:

Column 24,
Line 42, after "groups, and about 15%," please delete "to bout 30%" and insert -- to about 30% -- in its place.

Signed and Sealed this

Fifteenth Day of June, 2004

JON W. DUDAS
*Acting Director of the United States Patent and Trademark Office*